(12) United States Patent
Ting et al.

(10) Patent No.: US 8,836,202 B2
(45) Date of Patent: Sep. 16, 2014

(54) PIEZOELECTRIC DEVICE SYSTEM PRODUCING BOTH VIBRATION AND ELECTRIC POWER

(71) Applicant: Chung-Yuan Christian University, Chung Li (TW)

(72) Inventors: Yung Ting, Chung Li (TW); Sheuan-Perng Lin, Chung Li (TW); Chia-An Wei, Chung Li (TW)

(73) Assignee: Chung-Yuan Christian University, Chung Li, Tao Yuan County (TW)

( * ) Notice: Subject to any disclaimer, the term of this patent is extended or adjusted under 35 U.S.C. 154(b) by 0 days.

(21) Appl. No.: 13/757,313

(22) Filed: Feb. 1, 2013

(65) Prior Publication Data

US 2013/0300258 A1    Nov. 14, 2013

(30) Foreign Application Priority Data

May 9, 2012    (TW) .............. 101116532 A (51) Int. Cl.
| | |
|---|---|
| H01L 41/09 | (2006.01) |
| H02N 2/18 | (2006.01) |
| H01L 41/08 | (2006.01) |
| H01L 41/107 | (2006.01) |
| B23H 1/02 | (2006.01) |
| B23H 7/26 | (2006.01) |
| A61N 1/32 | (2006.01) |

(52) U.S. Cl.
CPC ............ *H02N 2/186* (2013.01); *H01L 41/0825* (2013.01); *H01L 41/107* (2013.01); *B23H 1/02* (2013.01); *B23H 7/26* (2013.01); *A61N 1/32* (2013.01)
USPC ............................................ 310/329; 310/328

(58) Field of Classification Search
USPC ........................................ 310/329, 339, 328
See application file for complete search history.

(56) References Cited

U.S. PATENT DOCUMENTS

| | | | |
|---|---|---|---|
| 4,197,478 A * | 4/1980 | Silvus, Jr. ................ | 310/316.01 |
| 7,579,757 B2 * | 8/2009 | Kulah et al. .................... | 310/339 |
| 8,410,667 B2 * | 4/2013 | Rastegar et al. .............. | 310/339 |
| 2006/0033406 A1 * | 2/2006 | Rastegar et al. .............. | 310/339 |

* cited by examiner

*Primary Examiner* — Derek Rosenau
(74) *Attorney, Agent, or Firm* — Muncy, Geissler, Olds & Lowe, P.C.

(57) ABSTRACT

A piezoelectric device system has a first piezoelectric element, a proof mass, a second piezoelectric element, and a microstructure output portion. The first piezoelectric element is oscillated by a power source. The proof mass is disposed between the first piezoelectric element and the second piezoelectric element, and transmits the vibration from the first piezoelectric element to the second piezoelectric element so as to make the second piezoelectric element move and generate power. The microstructure output portion is disposed on the other side of the second piezoelectric element opposite to the proof mass for transmitting the power generated by the second piezoelectric element.

5 Claims, 10 Drawing Sheets

PIEZOELECTRIC DEVICE SYSTEM PRODUCING BOTH VIBRATION AND ELECTRIC POWER

BACKGROUND OF THE INVENTION

1. Field of the Invention

The present invention relates to a piezoelectric device system; more particularly, the present invention relates to a piezoelectric device system producing both vibration and electric power.

2. Description of the Related Art

The piezoelectric effect refers to conversion between electrical energy and mechanical energy. The direct piezoelectric effect was first discovered in 1880 by the brothers Pierre Curie and Jacques Curie. In 1947, the discovery by S. Roberts of the effect of a direct current electric field on the remanent polarization of Barium Titanate (BaTiO3) ceramics inspired research into the piezoelectric properties of ceramic materials and their possible applications.

The direct piezoelectric effect is the process of converting mechanical energy into electrical energy. When physical pressure is applied to a piezoelectric material, the electric dipole moment of the material is shortened due to the compression. At this time, in order to resist this change, the piezoelectric material generates equivalent positive and negative charges on a corresponding surface of the material so as to maintain its original shape. The generation of polarization due to deformation is called the "direct piezoelectric effect".

The inverse piezoelectric effect is the process of converting electrical energy into mechanical energy. When an electric field (voltage) is applied to the surface of the piezoelectric material, the electric dipole moment is elongated due to the electric field effect, so the piezoelectric material extends along the direction of the electric field in order to resist this change. The generation of mechanical deformation by an electric field is called the "inverse piezoelectric effect".

In general, a piezoelectric element is commonly applied for simply converting mechanical energy into electrical energy, or for converting electrical energy into mechanical energy. However, since the piezoelectric element can utilize a voltage to generate vibration, and can further utilize the vibration (for causing deformation) to generate electric power, a system can be designed with two piezoelectric elements, wherein one is used as a vibration source, and the other is used as a power source, such that various applications can be implemented by utilizing the vibration property to generate electric power.

SUMMARY OF THE INVENTION

It is an object of the present invention to provide a piezoelectric device system for producing both vibration and electric power functions by utilizing two piezoelectric elements.

To achieve the abovementioned objects, the present invention provides a piezoelectric device system, which comprises a first piezoelectric element, a proof mass, a second piezoelectric element, and a microstructure output portion.

The first piezoelectric element generates vibration via a power source. The proof mass is disposed between the first piezoelectric element and the second piezoelectric element. The proof mass transmits the vibration from the first piezoelectric element to the second piezoelectric element, so as to make the second piezoelectric element move and generate power. The microstructure output portion is disposed on the other side of the second piezoelectric element opposite to the proof mass for transmitting the power generated by the second piezoelectric element. The spring is used to moderate the frequency $\omega_1$ in the input to satisfy the output specification of frequency $\omega_2$.

In a first embodiment of the present invention, the microstructure output portion is applicable for micro electrical discharge machining (micro-EDM). It generates an output power of 1~8 W with a current peak of 14~130 mA for electrical discharge machining and a vibration frequency of 1~500 KHz for dreg removing.

In a second embodiment of the present invention, the microstructure output portion is applicable for electrical stimulation ultrasound. It generates an output power of 3~4 W with a current peak of 30~100 mA for electrotherapy and a vibration frequency of 10~15 KHz for ultrasonic vibration.

In the second embodiment, the piezoelectric device system preferably comprises a driving controller electrically connected to the first piezoelectric element so as to make the first piezoelectric element generate a plurality of resonant frequencies, wherein the resonant frequencies include 1 MHz, 1.26 MHz, and 1.5 MHz.

Other objects, advantages, and novel features of the invention will become more apparent from the following detailed description when taken in conjunction with the accompanying drawings.

BRIEF DESCRIPTION OF THE DRAWINGS

These and other objects and advantages of the present invention will become apparent from the following description of the accompanying drawings, which disclose several embodiments of the present invention. It is to be understood that the drawings are to be used for purposes of illustration only, and not as a definition of the invention.

In the drawings, wherein similar reference numerals denote similar elements throughout the several views.

DETAILED DESCRIPTION OF THE PREFERRED EMBODIMENT

Figure 1:
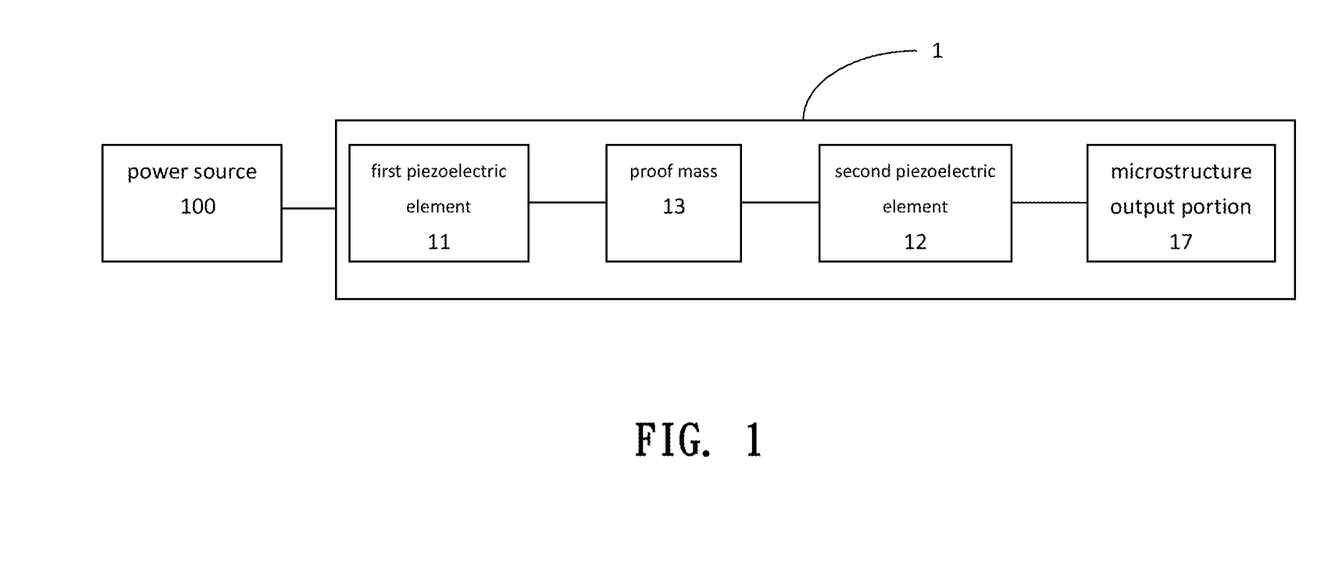
FIG. 1 illustrates a block diagram of a piezoelectric device system producing both vibration and electric power according to the present invention

Please refer to FIG. 1, which illustrates a block diagram of a piezoelectric device system producing both vibration and electric power according to the present invention. The piezoelectric device system 1 of the present invention comprises a first piezoelectric element 11, a proof mass 13, a second piezoelectric element 12, and a microstructure output portion 17. The first piezoelectric element 11 is used for generating vibration via a power source 100. An electric field (voltage) is applied to the first piezoelectric element 11. That is, to utilize the inverse piezoelectric effect, because the electric dipole moment will be elongated due to the electric field effect, the first piezoelectric element 11 will extend along the direction of the electric field in order to resist such change, and therefore the mechanical deformation will generate the vibration. Because the theory of vibration of the piezoelectric element is known by those skilled in the art, there is no need for further description.

The proof mass 13 is disposed between the first piezoelectric element 11 and the second piezoelectric element 12. The proof mass 13 transmits the vibration from the first piezoelectric element 11 to the second piezoelectric element 12, so as to make the second piezoelectric element 12 move and generate power. That is, to utilize the direct piezoelectric effect for the second piezoelectric element 12, when the physical pressure (displacement) generated by the vibration is applied to the second piezoelectric element 12, the electric dipole moment of the second piezoelectric element 12 will be shortened due to the compression, and therefore will generate equivalent positive and negative charges on its surface, so as to keep the original shape and thus generate the power.

The first piezoelectric element 11 generates vibration $X=A \sin \omega t$, and the second piezoelectric element 12 generates vibration $X'=A' \sin(\omega_n t-\phi)$, wherein the relative displacement between the first and second piezoelectric elements 11 and 12 is $D=A'-A$, calculated according to the following equation:

$$D = \frac{m_2 \omega_n A}{C + K_s^2 (R_{load} + R_{int})}$$

where $K_s$ is the spring constant (if any); C is the damping coefficient; $m_2$ is the mass of the second piezoelectric element 12; and $\omega_n \sqrt{K_s, m_2}$, which is the resonant frequency of the second piezoelectric element 12.

The second piezoelectric element 12 generates the direct piezoelectric effect because of the vibration with relative displacement, wherein the generated current and power are calculated according to the following equations:

$$i = \frac{V_{bmf}}{R_{load} + R_{int}} = \frac{K_{me}}{R_{load} + R_{int}} \omega_n Z\cos(\omega_n t - \phi); P_{out} = i^2 R_{load}$$

where $K_{me}$ is the mechanical coupling coefficient; $V_{bmf}$ is the back electromotive force ($V_{bmf}=K_{me}\dot{D}$); $R_{load}$ is the load resistance; and $R_{int}$ is the material impedance.

The microstructure output portion 17 is disposed on the other side of the second piezoelectric element 12 opposite to the proof mass 13, and is used for transmitting the power generated by the second piezoelectric element 12.

Figure 2:
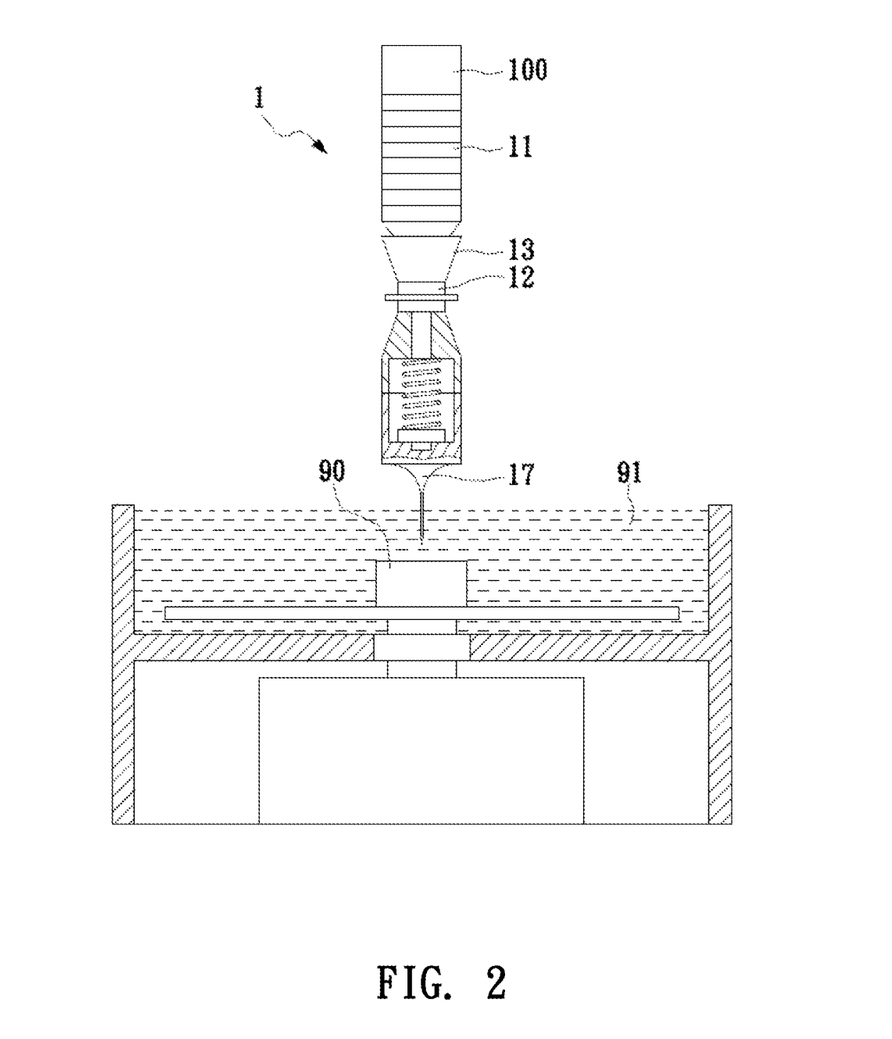
FIG. 2 illustrates a schematic drawing of the piezoelectric device system according to the embodiment of FIG. 1.

Please refer to FIG. 2, which illustrates a schematic drawing of the piezoelectric device system according to the embodiment of the FIG. 1. In the embodiment, the microstructure output portion 17 is applicable for micro electrical discharge machining (micro-EDM), as it generates an output power of 1~8 W with a current peak of 14~130 mA, and a vibration frequency of the first piezoelectric element 11 is around 1 MHz.

The theory of micro-EDM utilizes the property that a metal conductor is electric-conductive, wherein one electrode is connected to a tool having electrode (such as the microstructure output portion 17 in this embodiment), and the other electrode is connected to a workpiece 90 that needs to be processed; then a working voltage is applied between the two metal electrodes, and the two electrodes are placed in a working fluid or a dielectric fluid 91, so as to generate a certain insulating effect. As a result, when the two electrodes are at a tiny distance (such as 40~50 μm), the insulation of the dielectric fluid 91 between the electrodes will be damaged due to the electric field effect. Because the electrodes of the two ends exceed a threshold voltage between the electrode and the workpiece, ionization will occur at the two ends, thereby generating discharge columns and causing a discharge behavior. Accordingly, thermal actions (such as ionization, fusion and evaporation) and mechanical functions (such as discharging and burst power) caused by the discharge behavior will remove the metal and therefore achieve the purpose of machining (such as cutting).

In micro-EDM, during electrical discharge machining, the surface of the workpiece 90 is etched to form a discharge crater. When the etched workpiece 90 contacts the working fluid 91, it will cool down and form molten particles, and a recast layer will be formed once the working fluid 91 cools down. In order to avoid the above situation, the vibration provided by the first piezoelectric element 11 will generate countless tiny, dense bubbles. As a result, when the dense bubbles collapse under pressure during the vibration, a strong impact (the partial pressure of which may reach thousands of atmospheric pressures) will be generated owing to the acceleration, and thus will cavitation be generated. Accordingly, the dust and particles attached to the surface, slits, and corners of the workpiece 90 can be cleaned. The vibration wave not only can accelerate the speed of the dust and particles but also can prevent the dust and particles from being attached to the cutting tool electrode, so as to prevent secondary discharge, abnormal discharge, or serious cutting tool wear. Furthermore, the vibration wave can also reduce the amount of the molten particles attached to the surface of the workpiece 90 that would otherwise form the recast layer. According to the above machining process, the size precision, shape precision, and surface roughness are obviously superior to those of the traditional art, wherein the machinable aperture reaches φ10 μm, the depth is 0.5~10 mm, the size precision is ±0.005~±0.01 mm, the surface roughness (Ra) is a micro hole of 3.2~0.10 μm.

Figure 3:
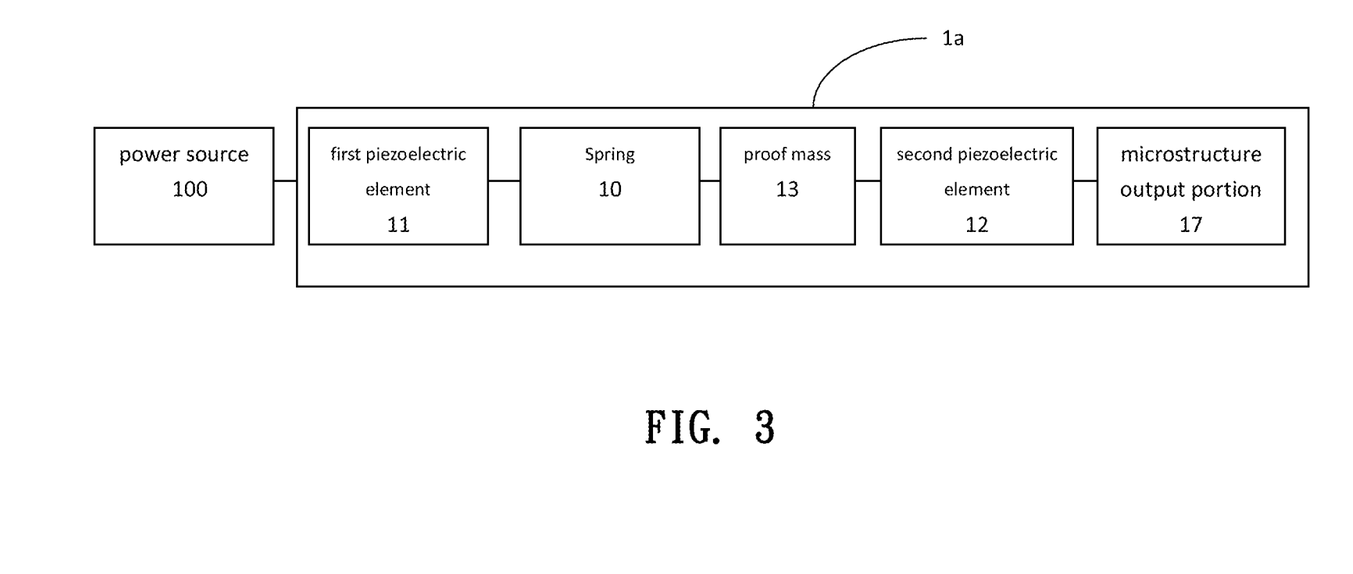
FIG. 3 illustrates a block diagram of the piezoelectric device system according to a preferred embodiment of the present invention.

Please refer to FIG. 3, which is similar to FIG. 1. The block diagram of FIG. 3 discloses a piezoelectric device system 1a further comprising a spring 10 accompany with the proof mass 13 so as to enhance the vibration.

The first piezoelectric element 11 generates vibration $X_1 = \overline{X}_1 \sin \omega_1 t$, and the second piezoelectric element 12 generates vibration $X_2 = \overline{X}_2 \sin(\omega_2 t-\phi)$. Because of the variation of displacement ($\overline{X}_1 \rightarrow \overline{X}_2$) and frequency ($\omega_1 \rightarrow \omega_2$) between the first and second piezoelectric elements 11 and 12, energy will be transmitted. The operating frequency $\omega_2$ of the second element is basically determined by the spring constant $K_s$ of the spring 10 and the mass of the second piezoelectric element 12 as well as the proof mass 13.

In another embodiment of the present invention, the microstructure is applicable for electrical stimulation ultrasound, as it generates an output power of 3~4 W with a current peak of 30~100 mA and a vibration frequency of 10~15 KHz.

Figure 3A:
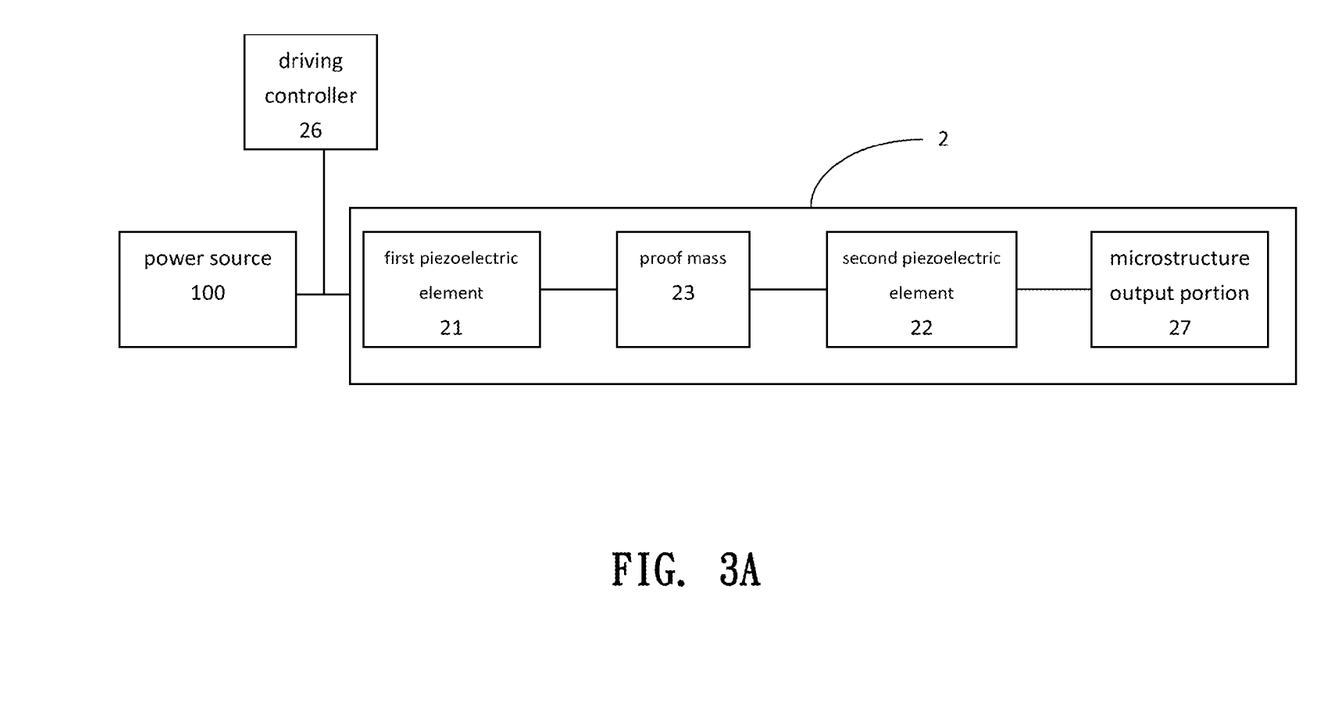
FIG. 3A illustrates a block diagram of the piezoelectric device system according to another preferred embodiment of the present invention.

Please refer to FIG. 3A, which illustrates a block diagram of the piezoelectric device system according to one embodiment of the present invention. The difference between FIG. 3 and FIG. 1 is that the piezoelectric device system 2 further comprises a driving controller 26. The driving controller 26 is electrically connected to the first piezoelectric element 21, so as to make the first piezoelectric element 21 generate a plurality of resonant frequencies. The resonant frequencies comprise 1 MHz, 1.26 MHz, and 1.5 MHz. Because the technique of generating a plurality of interlaced resonant frequencies by utilizing a driving controller (such as a waveform generator, a regulator, or an amplifier circuit) is well known, there is no need for further description.

Figure 3B:
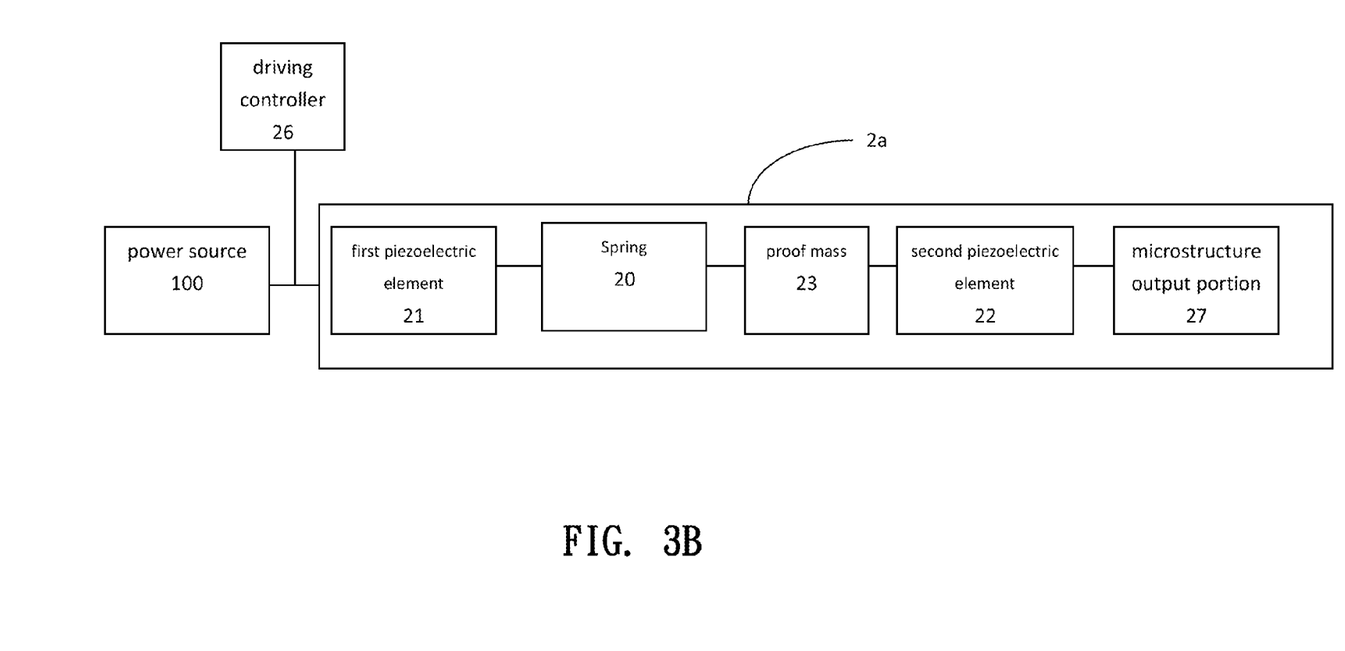
FIG. 3B illustrates a block diagram of the piezoelectric device system according to further preferred embodiment of the present invention.

Similarly, please refer to FIG. 3B. In this embodiment, the piezoelectric device system 2a may further comprise a spring 20 accompany with the proof mass 23 so as to enhance the vibration or change the frequency.

Figure 4:
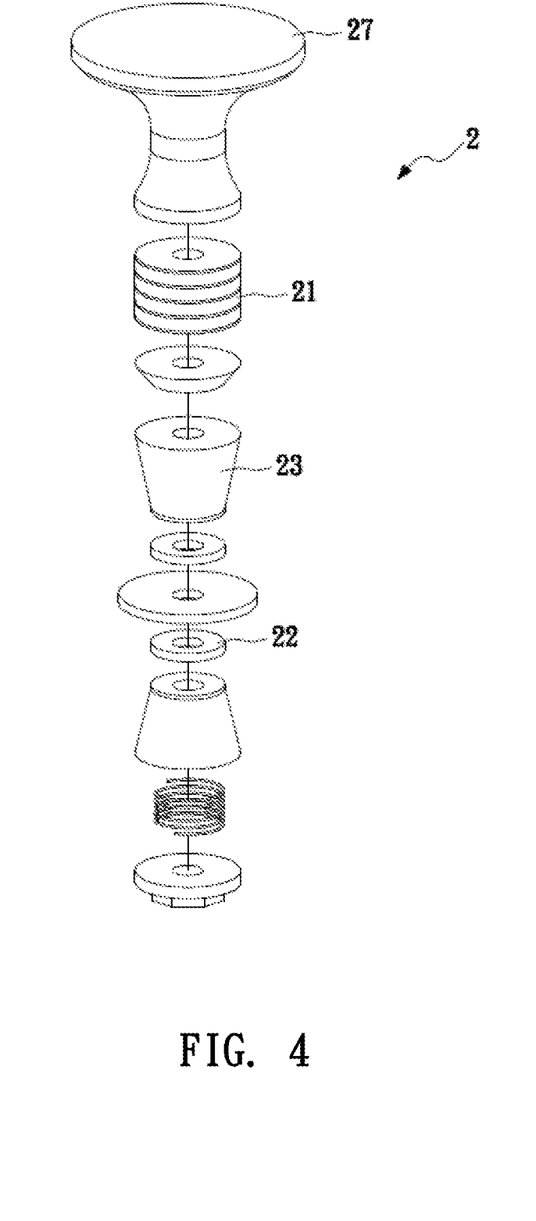
FIG. 4 illustrates a schematic drawing of the piezoelectric device system according to the embodiment of FIG. 3A.
Figure 6:
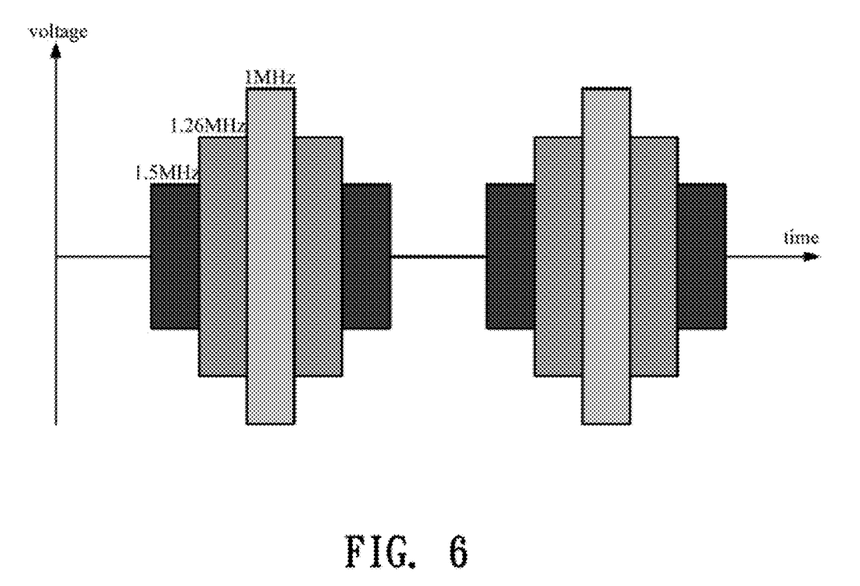
FIG. 6 illustrates a diagram showing the result of combining three resonant frequencies by means of a frequency-hopping spread spectrum (FHSS) technique according to the second embodiment of the present invention.

Please refer to FIG. 4, which illustrates a schematic drawing of the piezoelectric device system according to the second embodiment of the present invention. Similar to the first embodiment, the first piezoelectric element 21 of the second embodiment is used for generating vibration via the power source 100, and can further utilize the driving controller 26 to generate a plurality of resonant frequencies. According to ANSYS analysis, the three resonant frequencies of 1 MHz, 1.26 MHz, and 1.5 MHz are generated, and they can be combined by means of a frequency-hopping spread spectrum (FHSS) technique to achieve the result shown in FIG. 6. Therefore, with regard to string waves at the three frequencies of 1 MHz, 1.26 MHz, and 1.5 MHz, a microprocessor is utilized to control the output frequency of the string waves in a periodic FHSS basis to achieve a frequency modulation (FM) effect.

The second piezoelectric element 22 of the embodiment is similar to that of the first embodiment, and is used for discharging. As a result, the embodiment of the present invention can be used as the electrical stimulation ultrasound for electrotherapy, wherein the first piezoelectric element 21 provides the vibration, the second piezoelectric 22 provides the power required for the electrotherapy, and the microstructure output portion 27 outputs the power.

Figure 5:
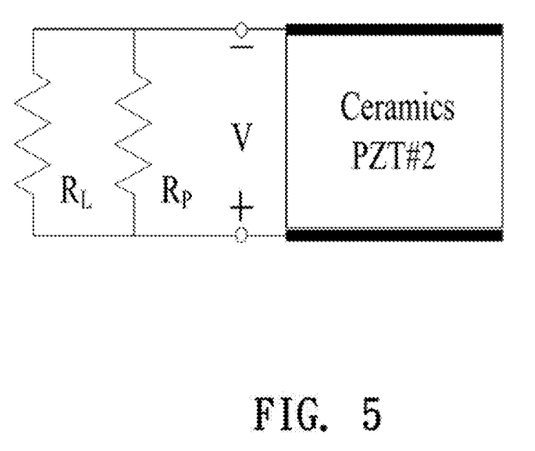
FIG. 5 illustrates an equivalent circuit to harvest the energy in the second piezoelectric element. According to the equivalent circuit, the output power is $P_{out}=V_{out}^2/R_{eq}$, $R_{eq}=(R_p//R_L)\approx R_L'$ where $R_p$ is the impedance of the ceramics and $R_L$ is the load resistance.

FIG. 5 illustrates an equivalent circuit to harvest the energy in the second piezoelectric element. According to the equivalent circuit, the output power is $P_{out}=V_{out}^2/R_{eq}$, $R_{eq}=(R_p//R_L)\approx R_L$, where $R_P$ is the impedance of the ceramics and $R_L$ is the load resistance.

Figure 7:
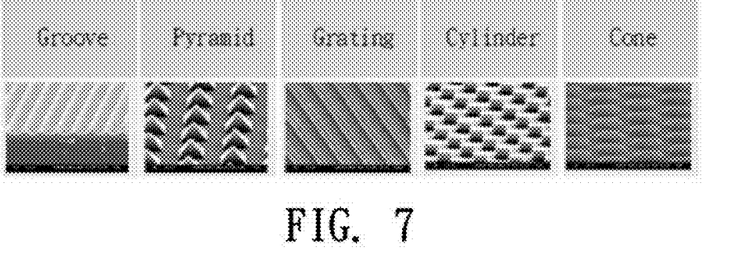
FIG. 7 illustrates several possible microstructures of the tip used for micro-EDM. Using sputtering deposition, copper or aluminum, for example, can be attached to the surface of microstructure as conductive media.
Figure 8:
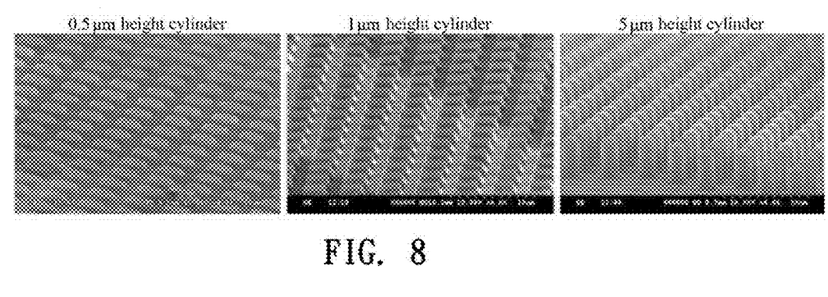
FIG. 8 illustrates several possible array-type of microstructures used for electrotherapy.

FIG. 7 illustrates several possible microstructures of the tip used for micro-EDM. Using sputtering deposition, copper or aluminum, for example, can be attached to the surface of microstructure as conductive media. FIG. 8 illustrates several possible array-type of microstructures used for electrotherapy.

Although the present invention has been explained in relation to its preferred embodiments, it is to be understood that many other possible modifications and variations can be made without departing from the spirit and scope of the invention as hereinafter claimed.

What is claimed is:

1. A piezoelectric device system, comprising:
a first piezoelectric element, used for generating vibration via a power source;
a proof mass, disposed on one side of the first piezoelectric element;
a second piezoelectric element, wherein the proof mass is disposed between the first piezoelectric element and the second piezoelectric element, and the proof mass transmits the vibration from the first piezoelectric element to the second piezoelectric element so as to make the second piezoelectric element move and generate power; and
a microstructure output portion, disposed on the other side of the second piezoelectric element opposite to the proof mass for transmitting the power generated by the second piezoelectric element.

2. The piezoelectric device system as claimed in claim 1, wherein the microstructure output portion is applied to micro electrical discharge machining (micro-EDM), as it generates an output power of 1~8 W with a current peak of 14~130 mA and a vibration frequency of 1~500 KHz.

3. The piezoelectric device system as claimed in claim 1, wherein the microstructure output portion is applied to electrical stimulation ultrasound, as it generates an output an output power of 3~4 W with a current peak of 30~100 mA for electrotherapy and a vibration frequency of 10~15 KHz for ultrasonic vibration.

4. The piezoelectric device system as claimed in claim 3, further comprising a driving controller electrically connected to the first piezoelectric element, so as to make the first piezoelectric element generate a plurality of resonant frequencies.

5. The piezoelectric device system as claimed in claim 4, wherein the resonant frequencies comprise 1 MHz, 1.26 MHz, and 1.5 MHz.

* * * * *